(12) United States Patent
Hansen

(10) Patent No.: US 9,061,116 B2
(45) Date of Patent: Jun. 23, 2015

(54) INTRODUCER ASSEMBLY AND SHEATH THEREFOR

(71) Applicant: Palle Munk Hansen, Bjaeverskov (DK)

(72) Inventor: Palle Munk Hansen, Bjaeverskov (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/787,027

(22) Filed: Mar. 6, 2013

(65) Prior Publication Data

US 2014/0005638 A1    Jan. 2, 2014

(30) Foreign Application Priority Data

Jun. 29, 2012 (GB) .................................. 1211578.8

(51) Int. Cl.
*A61M 25/01* (2006.01)
*A61M 25/00* (2006.01)
*A61M 25/06* (2006.01)
*A61F 2/966* (2013.01)

(52) U.S. Cl.
CPC ............ *A61M 25/01* (2013.01); *A61M 25/0053* (2013.01); *A61M 25/0662* (2013.01); *A61F 2/966* (2013.01)

(58) Field of Classification Search
CPC ............ A61M 25/01; A61M 25/0053; A61M 25/0662; A61F 2/966
USPC ............ 604/523–527, 164.01, 164.1, 164.12, 604/170.02; 606/108, 191; 623/1.11
See application file for complete search history.

(56) References Cited

U.S. PATENT DOCUMENTS

| 5,725,571 | A | 3/1998 | Imbert et al. |
| 7,470,282 | B2 | 12/2008 | Shelso |
| 8,303,617 | B2 * | 11/2012 | Brady et al. .................. 606/200 |
| 2004/0064130 | A1 * | 4/2004 | Carter .......................... 604/523 |
| 2008/0132906 | A1 | 6/2008 | Rasmussen |
| 2009/0177260 | A1 | 7/2009 | Aggerholm |

FOREIGN PATENT DOCUMENTS

| WO | WO 0135841 A1 * | 5/2001 |
| WO | WO 2004/080504 A2 | 9/2004 |
| WO | WO 2006/113863 A2 | 10/2006 |

* cited by examiner

*Primary Examiner* — Aarti B Berdichevsky
*Assistant Examiner* — Bradley Osinski
(74) *Attorney, Agent, or Firm* — Brinks Gilson & Lione

(57) ABSTRACT

An introducer assembly (10) includes a sheath (18) having a proximal portion (26) with a greater wall thickness and a distal portion (30) with a smaller wall thickness. A transition portion (28) may be provided to give a gradual transition between the proximal and distal portions (26, 30). The outer surface (32) of the sheath (18) has a substantially smooth and preferably even form and preferably constant diameter. The sheath (18) can thus have a greater flexibility at its distal end that at its proximal end, to improve trackability and thus to facilitate deployment of an implantable medical device (16) carried by the introducer (10). The smooth outer surface (22) prevents snagging of the introducer assembly (10) during and after the deployment procedure.

14 Claims, 1 Drawing Sheet

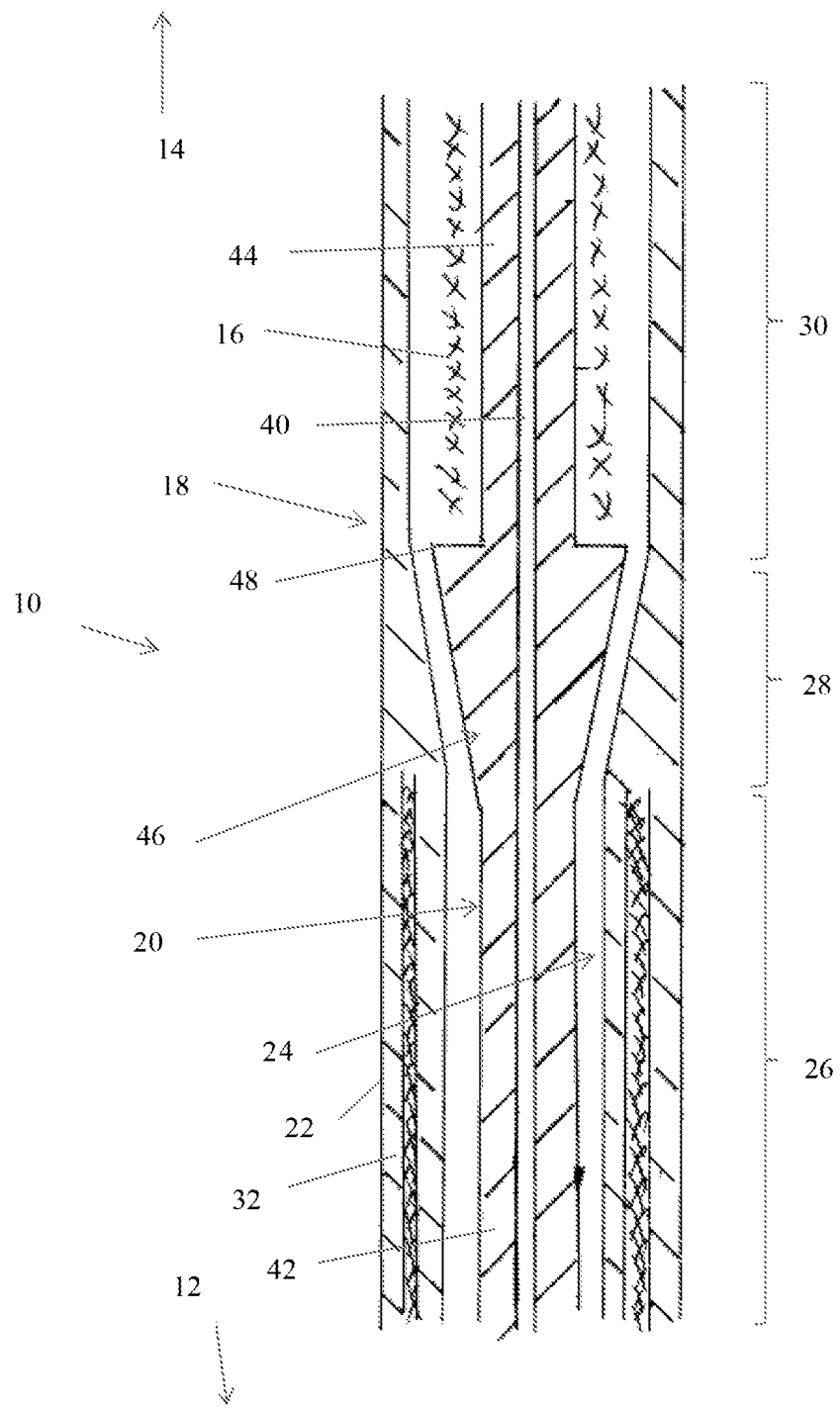

INTRODUCER ASSEMBLY AND SHEATH THEREFOR

This application claims the benefit of the filing date of United Kingdom (GB) patent application number 1211578.8, filed Jun. 29, 2012, which is hereby incorporated by reference herein.

TECHNICAL FIELD

The present invention relates to a sheath or catheter for a medical device and to an introducer assembly.

BACKGROUND OF THE INVENTION

Sheaths and catheters are commonly used, particularly in endoluminal procedures. It is important that such sheaths have a good longitudinal strength in order to ensure that the sheath can be pushed through a patient's vasculature and that the sheath and its contents do not compress longitudinally as the sheath is guided into position.

In addition to needing to have longitudinal strength, such sheaths and catheters must be sufficiently flexible so as to be able to follow the curves of the patient's vasculature, but also to be kink resistant. Kinking of the sheath can lead to damage of the contents of the sheath, inability to extract the contents within the patient and generally to an abortive medical procedure.

For this reason, sheaths in particular often have complex structures with embedded strengthening elements such as coils or metal braids. The risk of kinking is reduced by having the strengthening structure extend substantially for the whole length of the sheath.

Although strengthening elements can be effective in minimising the risk of kinking, they can lead to loss of flexibility and as a result loss of trackability, that is ability of the sheath to follow the curves in a patient's vessels. Furthermore, they can lead to increased sheath diameter particularly at the distal end of the sheath, which typically must house components which have a greater diameter than the other elements in the introducer assembly such as pusher catheters, guide wire catheters and the like.

Examples of known sheath structures can be found, for instance, in WO-2006/113863, US-2008/0132906, US-2009/0177260, U.S. Pat. No. 7,470,282, U.S. Pat. No. 5,725,571 and WO-2004/080504.

SUMMARY OF THE INVENTION

The present invention seeks to provide an improved sheath or catheter (hereinafter referred to as a sheath) and an improved introducer assembly.

According to an aspect of the present invention, there is provided a sheath for an introducer assembly including proximal and distal ends, an outer surface and an internal surface providing a lumen within the sheath extending between said proximal and distal ends; said lumen formed by said internal surface including a proximal section proximate the proximal end of the sheath and a distal section proximate the distal end of the sheath; the proximal section having a smaller diameter than a diameter of the distal section; wherein the outer surface of the sheath has a substantially constant diameter or a substantively constantly varying diameter between the proximal and distal ends of the sheath.

This structure provides a sheath with a smaller wall thickness at the distal end of the sheath, which increases the flexibility of the sheath at that end and therefore better deployment of medical devices or equipment particularly in a curved portion of a patient's vessel, as well as facilitating the endoluminal passage of the sheath to the point of treatment. The outer surface of the sheath can be substantially smooth, thereby avoiding risk of catching the sheath in a vessel during its insertion into a patient.

The term "sheath" used herein is intended to encompass sheaths and catheters, although the preferred embodiments are directed to sheaths which form the outermost component of an introducer assembly and which holds the other elements of the assembly as well as a medical device carried thereby.

Preferably, there is provided a transition section between the distal and proximal sections of the sheath. A transition section can provide a more gradual change between the two different sections of the sheath and thus reduce the risk of kinking. However, as is described below, embodiments are contemplated in which the internal components of the introducer assembly provide support for the distal end of the sheath.

It is preferred that the transition section has a tapering internal diameter from the proximal section to the distal section. A taper of this nature will provide a gradual change between the two sections of the sheath, ideal for reducing the risk of kinking as well as assisting in the curving of the stiffer portion of the sheath.

In an embodiment, the transition section has a length from about 10 mm to about 200 mm, more preferably from about 20 mm to about 150 mm. A transition section with a length within this range has been found to provide optimum characteristics. Devices have been tested with sheaths having outer diameters of 2-4 French and a transition region of 20 to 120 mm, as well as with sheaths having diameters of 6 French or more and a transition region of 20 mm to 150 mm and longer.

Advantageously, there is provided a structural element extending within at least a part of proximal section and a least part of the transition section. The structural element may be a strengthening element, for instance.

In an embodiment, the sheath has a structure which is different in the proximal section than in the distal section. Preferably, the sheath includes a structural element within the proximal section, which may be a strengthening element such as a braid or coil or a layer of material. The layer may be of polymeric material or metal or fibre.

Preferably, the distal section of the sheath is free of strengthening elements and may be formed as a single layer of material. The distal section need not have significant longitudinal strength or kink resistance per se, particularly when this holds a medical device or other component therewithin. In this regard, the distal section may constitute a device holding section of the sheath.

According to another aspect of the present invention, there is provided an introducer assembly including a sheath and a carrier element disposed in the sheath; the sheath including proximal and distal ends, an outer surface and an internal surface providing a lumen within the sheath extending between said proximal and distal ends; said lumen formed by said internal surface including a proximal section proximate the proximal end of the sheath and a distal section proximate the distal end of the sheath; the proximal section having a smaller diameter than a diameter of the distal section; wherein the outer surface of the sheath has a substantially constant diameter or a substantively constantly varying diameter between the proximal and distal ends of the sheath.

Advantageously, the carrier element includes a pusher element.

In the preferred embodiment, the sheath includes an internal transition region and the pusher element is provided with a pusher head, which pusher head has an outer surface of a shape equivalent to a shape of the transition region of the sheath. The provision of an internal component which has a shape equivalent to that of the transition region can provide radial support to the sheath and also increase longitudinal strength by ensuring that a device held within the distal end of the introducer assembly cannot slide backwards during the deployment process, in that the pusher head will be unable to slide further within the sheath.

In an embodiment, the pusher head is frusto-conical.

Advantageously, the carrier element includes a proximal section of outer diameter substantially equivalent to the inner diameter of the proximal section of the sheath.

BRIEF DESCRIPTION OF THE DRAWING

Embodiments of the present invention are described below, by way of example only, with reference to and as illustrated in the accompanying drawing, in which the sole FIGURE is a cross-sectional view of a portion of an introducer assembly according to a preferred embodiment of the present invention.

DESCRIPTION OF THE PREFERRED EMBODIMENTS

It is to be understood that the components shown in the FIGURE are not to scale and are enlarged for the purposes of clarity of disclosure. The person skilled in the art will be familiar with the typical and suitable dimensions for these components.

Referring to the FIGURE, there is shown a longitudinal cross-sectional view of a part of an introducer assembly 10 according to a preferred embodiment of the present invention. The proximal end 12 of the introducer assembly 10 extends towards the left in the view shown and typically terminates at an external manipulation unit which includes haemostatic valves, ports for flushing fluid, a luer fitting for receiving a guide wire and so on. These components are conventional in the art and therefore not described in any further detail herein.

The distal end 14 of the introducer assembly 10, which is towards the right in the FIGURE, typically terminates with a dilator tip, again of known form. In addition, the introducer assembly 10, when of a form used for deployment of an implantable medical device such as a stent 16, may include elements for retaining the medical device 16 in a radially compressed form, including for example restraining wires, restraining devices or other release elements. These components are well known in the art and do not affect the elements taught herein. They are therefore not shown in the FIGURE or described as they will be readily apparent to the person skilled in the art.

The introducer assembly 10 includes a sheath 18, described in detail below, a pusher element 20 in this embodiment designed to carry an implantable medical device 16, and other components typically associated with such assemblies. As mentioned above, the device 16 could be a stent, a stent graft or any other medical device able to be carried by the introducer assembly. It is to be understood also that the introducer assembly could be used for the deployment of other medical elements including, for example, treatment tools, diagnostic or measuring tools and so on. In this case, the assembly may include a different design of pusher or carrier element and may in some applications be used simply as a catheter for the introduction of medical tools or medical agents.

The sheath 18 shown in the FIGURE is the preferred embodiment of sheath taught herein. In particular, the sheath 18 has an outer circumferential surface 22 which has a substantially constant diameter from the proximal end 12 to the distal end 14 of the introducer assembly 10. By contrast, the sheath 18 has an internal surface 24, which is in the preferred embodiment substantially circular in transverse cross-section as is the outer surface 22. However, the internal surface 24 has different diameters along the length of the sheath 18. More specifically, the internal surface 24 has a first portion 26 of a first diameter, a second portion 28 of a diameter which gradually changes and a third portion 30 having a diameter greater than the first portion 26. In other words, the sheath 18 has a first, greater, wall thickness along portion 26, a gradually reducing wall thickness along portion 28 and is thinnest along portion 30.

The first portion 26 also includes embedded within the thickness of the wall thereof a strengthening element 32, which may be a braid or helical coil. The strengthening element 32 preferably extends all the way to the proximal end 12 of the sheath 18 and advantageously is mechanically coupled to the manipulation unit so as to give the proximal end of the sheath 18 enhanced strength over the entirety of the length of the portion 26. The strengthening element 32 may terminate at the end of the portion 26, that is before the transition zone 28, but it is preferred that the strengthening element 32 extend partially within the transition portion 28, particularly across the thicker section of the transition portion.

In contrast, for the preferred embodiments, the distal portion 30 has no strengthening element embedded therewithin. It is preferred that the distal portion 30 is made of a single layer of material, although it is not excluded that this could be a multi-layer structure of flexible material.

It is preferred that the portion 30 is of a length equivalent to the length of the implantable medical device 16. Portion 30, however, could be longer than the length of the implantable medical device 16, for instance if it desired to have a longer length of the introducer assembly with greater flexibility than the remainder of the sheath 18. The portion 30 could have a length from a few centimeters to some tens of centimeters.

The transition portion 28 preferably has a length of between about 10 mm and about 200 mm, most preferably between about 20 mm and about 150 mm. A transition zone 28 of such dimensions can ensure a smooth change in flexibility of the sheath 18 from the proximal portion 26 to the distal portion 30. The skilled person will appreciate that these dimensions will be dependent upon the outer diameter 22 of the sheath 18 and thus the intended medical application of the introducer assembly 10 (typically the ultimate size of the vessel within which the introducer assembly 10 is to be deployed).

In this regard, for a sheath having an outer diameter of 2 mm, the portion 26 may have a wall thickness of 0.6 to 0.7 mm, the distal portion 30 may have a thickness of 0.3 to 0.4 mm and the transition portion a length of around 20 to 150 mm. The difference in wall thickness may be 1:2 or greater, for instance 1:3, for a sheath of outer diameter up to around 6 French. A larger diameter sheath may have a larger difference in wall thickness of these two regions.

The pusher rod 20 shown in this embodiment is a generally cylindrical tube having a lumen 40 therein for receiving a guidewire (not shown) of conventional type. The lumen 40 will extend for the entire length of the pusher rod 20 and of the introducer assembly 10. The dilator 10 (not shown) will also include an equivalent lumen so that the guidewire can pass beyond the end of the dilator 10.

The pusher assembly 20 includes a proximal portion 42 which resides within a proximal portion 26 of the sheath 18. It will be appreciated that the proximal portion 22 may have an outer diameter which is only slightly smaller than the inner diameter of the proximal portion 26 of the sheath 18. The pusher rod 20 also includes a distal portion 44 which carries the implantable medical device 16. The distal portion 44 will therefore have an outer diameter which is somewhat less than the inner diameter of the distal portion 30 of the sheath 18 in order to leave a space for accommodating the implantable medical device 16. It is, as is known in the art, it is preferable that the components in the assembly 10 are a snug fit and thus the space between the distal portion 44 of the pusher rod 20 and the inner surface of the distal portion 30 of the sheath 18 should be just enough to accommodate the implantable medical device 16.

At the transition portion 28, the pusher rod 20 includes a frusto-conical portion 46 which has an outer surface of a shape consistent with, preferably generally the same as, the inner surface of the transition portion 28 of the sheath 18. The portion 46 of the pusher rod 20 may be a snug fit in the transition portion 28. The portion 46 of the pusher rod 20 ends with an annular shoulder 48 for providing a support for the implantable medical device in the longitudinal direction of the assembly 10. In some embodiments, the shoulder 48 may be on a cylindrical section which then tapers in frusto-conical manner.

It is to be understood that the portion 46 of the pusher rod 20 could have any shape which abuts against and is held by the inner surface of the tapering section 28. It could, for instance, have an outer surface which only partially reflects the inner surface of the tapering section 28.

It will be apparent that with this design and pusher rod 20, the pusher rod cannot be moved in a proximal direction, that is towards the end 12 of the introducer assembly 10 as it is unable to fit within the narrow diameter portions 26, 28 of the sheath 18. This prevents the medical device 16 from being pushed into the sheath 18 as the introducer assembly 10 is passed through a patient's vasculature. On the other hand, the pusher rod 20 can be moved in a distal direction of the assembly 10, so as to push the implantable medical device 16 and the distal portion 44 of the pusher rod 20 out of the sheath 18 (in practice being achieved by pulling the sheath 18 backwards in a proximal direction). Such relative movement between the sheath 18 and the pusher rod 20 enables deployment of the medical device 16, and in a manner known in the art.

Having regard to the deployment of the introducer assembly 10, given that the distal portion 30 of the sheath 18 has a thinner wall than the proximal portion 26, the distal end of the sheath 18 is more flexible, thus conferring increased flexibility to the distal end of the introducer assembly 10. This increased flexibility makes it easier for the introducer assembly 10 to be fed through tortuous vasculature of a patient and also makes it easier to locate the distal end of the introducer assembly 10 within a curved lumen. In other words, the distal end 30 of the assembly improves trackability of the assembly 10.

On the other hand, the proximal portion 26 of the sheath 18, which typically, is by far the greatest proportion of the overall length of the sheath 18, is relatively stiffer than the distal portion 30. This increased stiffness provides greater pushability of the introducer assembly 10. The transition portion 28 provides a gradual change in flexibility of the sheath 18, thereby assisting in the trackability of the remainder of the assembly 10 and also in reducing the chance of kinking of the sheath 18.

Moreover, the outer surface 22 of the sheath 18 is substantially smooth, which facilitates the deployment of the introducer assembly 10 within a patient and avoids snagging of the introducer assembly inside a patient's vasculature and/or against any device already located therewithin.

The preferred embodiment has an outer surface which is of consistent diameter throughout the length of the sheath, 18 such that the sheath 18 has the same outer diameter at the distal end as at its proximal end. Another embodiment provides a slight taper to the outer surface 22 of the sheath 18, such that the sheath 18 has a slightly larger diameter at its proximal end than at its distal end. Even so, it is preferred that the outer surface 22 is smooth throughout the length of the sheath 18, in particular over the proximal portion 26, transition portion 28 and the major part of the distal portion 30, which is inserted into a patient. In other words, any change in the outer diameter is gradual and even along the length of the sheath 18.

In some instances it is not necessary to have a transition portion 28 to the sheath 18, in which case the proximal and distal portions 26, 30 of the sheath 18 will be directly adjacent one another. Kinking can be reduced by means of components within the introducer assembly 10, for instance by means of a particular design of pusher rod 20 which may act as a transition element. This may, for example, be by means of a pusher head having a proximal shoulder equivalent to but opposite the distal shoulder 48 and which fits against an abrupt change in the internal diameters, surfaces 24, of the sheath 18.

Similarly, the transition zone 28 may have a stepped internal surface rather than a smooth internal surface as shown in the FIGURE.

The preferred embodiment described above has a sheath 18 with a round internal cross-section. Other embodiments may have an internal surface which is non-round, for example oval or even polygonal.

The preferred embodiment described above has a strengthening element 32 which is made of a metal or metallic material. Other embodiments may have a strengthening element made of a different material including polymers, which can increase the flexibility of the sheath 18 and thus of the introducer assembly 10. Moreover, as explained above, the distal end 30 of the sheath 18 may be provided with some strengthening elements (for instance an extension of the strengthening element 32), although for the preferred embodiment the distal end 30 is free of any additional strengthening elements.

Sheath 18 can be made of conventional materials known in the art, such as polyethylene, polyethene, polyether block amide (such as peebax), polyurethane, poly ether ketone (peek), polyamide (such as nylon) and so on. The inner lumen of the sheath may be formed on a mandrel, may be drilled out or may be provided by two or more sections of tubing bonded to one another.

It is to be understood that the features of the dependent claims may be combined with one another, as indeed they are in the embodiments described above, as if the claims were written in multiple dependent form.

The invention claimed is:

1. An introducer assembly, comprising:
   a sheath including proximal and distal ends, an outer surface and an internal surface providing a lumen within the sheath extending between said proximal and distal ends;
   a pusher rod disposed within said lumen of said sheath, said pusher rod comprising a portion that forms a shoulder;
   wherein said lumen formed by said internal surface includes a proximal section and a distal section, the proximal section extending proximally from the portion that forms the shoulder, the distal section extending distally from the shoulder;
   wherein the lumen further comprises an inner diameter, the inner diameter of the proximal section being smaller than the inner diameter of the distal section; wherein a length of the sheath extending from the proximal section to the distal section has a constant outer diameter or a constantly varying outer diameter, wherein a first portion of the length extends at least partially into the proximal section and a second portion of the length extends at least partially into the distal section;

a strengthening element comprising a braid or a helical coil embedded within a wall of the proximal section and no strengthening element embedded within a wall of said distal section;

wherein the shoulder has a larger diameter than said inner diameter of said proximal section; and an implantable medical device disposed within said distal section, said shoulder pushing against said implantable medical device to deploy said implantable medical device as said sheath and said pusher rod are moved relative to each other.

2. The introducer assembly according to claim 1, wherein said lumen is provided a transition section between the distal and proximal sections of the sheath.

3. The introducer assembly according to claim 2, wherein said transition section has a tapering diameter from the smaller diameter of the proximal section to the diameter of the distal section.

4. The introducer assembly according to claim 2, wherein the transition section has a length from 10 mm to 200 mm.

5. The introducer assembly according to claim 2, wherein the transition section has a length from 20 mm to 150 mm.

6. The introducer assembly according to claim 2, wherein the strengthening element is also embedded within at least a portion of the transition section.

7. The introducer assembly according to claim 1, wherein the sheath has a structure which is different in the proximal section than in the distal section.

8. The introducer assembly according to claim 1, wherein the distal section is a single layer of material.

9. The introducer assembly according to claim 1, wherein the distal section constitutes a device holding section of the sheath.

10. The introducer assembly according to claim 1, wherein the length extends from the proximal end of the sheath to the distal end of the sheath.

11. An introducer assembly including a sheath and a carrier element disposed in the sheath, the carrier element comprising a portion that forms a shoulder; the sheath including proximal and distal ends, an outer surface, a length extending between said proximal and distal ends, and an internal surface providing a lumen within the sheath extending between said proximal and distal ends; said lumen formed by said internal surface including a proximal section extending proximally from the portion that forms the shoulder and a distal section extending distally from the shoulder; wherein the lumen further comprises an inner diameter, the inner diameter of the proximal section being smaller than the inner diameter of the distal section; wherein a length of the sheath extending from the proximal section to the distal section has a constant outer diameter or a constantly varying outer diameter, wherein a first portion of the length extends at least partially into the proximal section and a second portion of the length extends at least partially into the distal section, and a strengthening element comprising a braid or a helical coil is embedded within a wall of the proximal section and no strengthening element is embedded within a wall of said distal section; wherein the shoulder has a larger diameter than said inner diameter of said proximal section; and an implantable medical device disposed within said distal section, said shoulder pushing against said implantable medical device to deploy said implantable medical device as said sheath and said carrier element are moved relative to each other.

12. An introducer assembly according to claim 11, wherein the sheath includes an internal transition region and the portion that forms the shoulder has an outer surface of a shape equivalent to a shape of the transition region of the sheath.

13. An introducer assembly according to claim 12, wherein the portion that forms the shoulder is frusto-conical.

14. The introducer assembly according to claim 11, wherein the length extends from the proximal end of the sheath to the distal end of the sheath.

* * * * *